(12) United States Patent
Sloth (10) Patent No.: US 6,432,058 B1
(45) Date of Patent: Aug. 13, 2002

(54) DEVICE FOR FASTENING IN THE CRANIAL BONE AND A KIT COMPRISING SUCH DEVICE

(76) Inventor: Erik Sloth, Adelvej 12, DK-8240, Risskov (DK)

( * ) Notice: Subject to any disclaimer, the term of this patent is extended or adjusted under 35 U.S.C. 154(b) by 0 days.

(21) Appl. No.: 09/508,795
(22) PCT Filed: Sep. 25, 1998
(86) PCT No.: PCT/DK98/00417
§ 371 (c)(1),
(2), (4) Date: Mar. 16, 2000
(87) PCT Pub. No.: WO99/16349
PCT Pub. Date: Apr. 8, 1999

(30) Foreign Application Priority Data

Sep. 26, 1997 (DK) .............................. 1105/97

(51) Int. Cl.⁷ ................................. A61B 8/14
(52) U.S. Cl. ...................... 600/462; 600/461
(58) Field of Search ................. 600/462, 561, 600/459, 461, 302, 424; 604/174, 9; 606/1, 130

(56) References Cited

U.S. PATENT DOCUMENTS

| | | | |
|---|---|---|---|
| 4,062,354 A | * 12/1977 | Taylor et al. | 600/32 |
| 4,246,908 A | * 1/1981 | Inagaki et al. | 600/561 |
| 4,328,813 A | 5/1982 | Ray | |
| 4,629,451 A | 12/1986 | Winters et al. | |
| 4,681,103 A | * 7/1987 | Boner | 606/1 |
| 4,705,499 A | * 11/1987 | Hooven | 604/9 |
| 4,805,634 A | 2/1989 | Ullrich et al. | |
| 5,054,497 A | 10/1991 | Kapp et al. | |

* cited by examiner

Primary Examiner—Marvin M. Lateef
Assistant Examiner—Ruby Jain
(74) Attorney, Agent, or Firm—Ladas & Parry (57) ABSTRACT

There is described a device for fastening in a bone, preferably the cranial bone. The device is usable for continual supervision without sterile conditions and without need for full anaesthesia. The device comprises a self-cutting screw which by means of a tool is placed in a boring that previously has been formed in the bone. The screw has an inner hollow space in which there is located a signal transducer, and at that end facing inwards towards the cranial cavity, the screw will be covered by signal penetrable membrane. When the screw is in its proper place, the "observation aperture" which is formed will have been closed, and, in practise, it appears that there is no risk of infections.

11 Claims, 8 Drawing Sheets

DEVICE FOR FASTENING IN THE CRANIAL BONE AND A KIT COMPRISING SUCH DEVICE

BACKGROUND OF THE INVENTION

The present invention relates to a device for fastening in a bone, preferably the cranial bone. Alternatively, the device may also be used in connection with tubular bones. The device is intended for use by momentary or continual supervision and examination of physical conditions in the inner cavities of the bone or behind the bone. Pathological conditions may be examined, as for example cerebral haemorrhage, oedema. squeezing off. extension of the ventricular system. dislocation of anatomical structures. tumours, accumulations of blood and liquid.

The invention is developed for and will especially be explained in connection with examination of accumulation in the cranial cavity and especially the content of this which is located behind the cranial bone. But it also gives advantages by use in tubular bones in order to examine developments in the bone marrow in the inner of the bone.

The invention furthermore relates to a kit comprising such a device, and which is intended for use by continual supervision and examination of physical conditions in the inner cavity of the bone or behind the bone. preferably in the cranial cavity.

Furthermore. the invention relates to the use of the device by continual supervision and examination of physical conditions in the cranial cavity.

Devices which have been used for examining physical conditions in the cranial cavity are known. However, the known devices are disadvantageous as they give a signal which occurs with a delay in relation to the physical condition which it is desired to supervise. Furthermore, it is a signal which indicates a stationary condition in the cranial cavity.

The known devices may also be disadvantageous by requiring greater surgical interventions necessitating sterile conditions and full anaesthesia. They are thus not suited for use in a hospital department where patients lie for observation.

The known devices and systems will be designed as explained in the following.

There is known a device whereby the pressure in the cranial cavity is supervised. This device may be placed without using full anaesthesia. The device may be removed without having to move the patient to a surgical department.

If a person is desired to be observed in order to detect physical conditions in the cranial cavity, for example, as a consequence of blows to the head, or as a supervision of a condition occurring after a surgical intervention, or for supervising a condition of sickness. it has been known to insert a screw through the cranial bone. This screw is hollow and has a point which passes through the membrane of the brain so that an open connection is established between the inner of the membrane of the brain and a manometer which is connected with the outer end of the screw situated outside the cranial bone.

On the manometer it is possible to register surpressure in the cranial cavity which is an indication of different subsequent damages which may occur in the cranial cavity. In practice, it has shown that these devices do not imply a great risk of infection. The intervention itself and the locating of the device, thus takes place without using full anaesthesia. However, the known system has a limitation as only an appearing increase in the pressure is occurring. It is not possible to determine a cause, which, for example, may be accumulations of blood or liquid in the cranial cavity.

Furthermore, the system will be tied to another drawback, because one will get an indication via the increase of pressure after an accumulation of blood or liquid has been built up through a certain time. Thus, a delay occurs before signal is received, and the signal is only an expression of a subsequent reaction.

Previously, there have been tests with measuring flow of blood to and from the cranial cavity. Through changes in the pressure in the blood supply vessels, it is possible to get an indication of a pressure built-up in the cranial cavity. This method is also disadvantageous by a delayed indication of a condition which is under development. This system is thus connected with the same drawbacks as mentioned above as one just get an indication of the symptom, and this indication comes with a delay.

For many years, a Doppler-ultrasound directly through the cranium has been used for measuring the rate of flow of blood. Because of the characteristic of the cranial bone, the ultrasound will have difficulty in penetrating and the measurements can therefore only be made in the temple region where the cranial bone is thinnest and allows penetration of ultrasound. With this access, it is not possible to achieve creation of an image of a technically usable quality.

Also, scanners are known, so-called CT-scanners and MR-scanners. Such scanners are, however, very costly in use. Furthermore, these are not devices which are practical in use in connection with beds in hospital departments where patients are admitted for observation.

As an expression of the need that has existed. it may be mentioned that in USA in 1992, 20 inhabitants out of 100,000 died because of so-called cranial traumas. The total number of severe cranial traumas is estimated to be about 5 times as large. The need for a supervision may thus be estimated to be several hundred thousand a year in the Western world. In spite of this need, there has until now not been proposed devices or methods for continual supervision with a cerebral image forming technique which is competitive in relation to the known scannings.

Previously, there has been proposed an equipment using ultrasound scanning of physical conditions in the cranial cavity. This equipment and the use thereof are described in International patent application WO 87/03190. This equipment is intended for mounting over a hole in the cranial bone formed for this purpose and is placed in a way so that it fits tightly to the cranial bone. However, this equipment and the described method are unfavourable as they require craniotomi, i.e. removal of a larger piece of bone. The equipment has to be used under full anaesthesia and under sterile conditions and is intended for use in connection with neurosurgical interventions in the cranial cavity. Use of the described equipment will thus be very demanding on resources, because of requirements of sterile conditions and requirements of full anaesthesia. This is the case with locating as well as the subsequent supervision situation.

The equipment is furthermore unfavourable as a risk of contamination occurs. In the system, there is used a transducer which in principle participates in the closing of the formed hole in the cranial bone. As the equipment comprises elements making possible access of different instruments to the cranial cavity, we are speaking about a complete system which cannot be said to be closed, and thereby a system which may be considered to be used under unsterile conditions.

The equipment furthermore requires complicated fastening in the opening formed in the cranial bone by means of a clamping technique. Even though the described equipment makes possible the creation of an image of physical conditions in the cranial cavity, it will not be suitable for use for continual supervision and examination of the cranial cavity on persons situated in unsterile hospital departments.

A holder that may be fastened in a bone, for example the cranium, is known from U.S. Pat. No. 4,681,103. This holder may be used for an ultrasound transducer. This holder is, however, open towards the inner of the cranium and may thus not be used outside a sterile area in a hospital. This holder and the equipment belonging to it in the form of an ultrasound transducer and a needle on the described apparatus, may thus not be used for supervision, but only to perform localisation of a spot by means of an ultrasound transducer in connection with a surgical intervention. After determining the positioning, a guide is adjusted in the holder. Subsequently, this guide is used as support for the needle. There is no precise indication of how to ensure a correct screwing of the holder into the bone.

From American U.S. Pat. No. 5,054,497 there is known an equipment which may be fastened in a bone, for example the cranial bone. In this equipment, there is no description of a possibility of supervision. The equipment is used in connection with the previously mentioned pressure measurement which is disadvantageous by giving a delayed indication of conditions in the brain. The described system will contain openings which do not make it usable in hospital sections outside sterile areas. The system is thus only usable for use in connection with operations and not for use by continual supervisions.

Thus, there exists a need for a technique making possible creation of an image for physical conditions in the cranial cavity. In order to achieve the best utility, there will especially be a need for an image forming technique making possible a three-dimensional creation of an image by scanning, and especially a scanning which may be performed continually without need for sterile conditions, full anaesthesia, etc. during the supervision, as this is very demanding on resources and work. Thus, there is need for an image forming technique which makes possible a scanning which may be performed continually at the bed of the patient in a non-sterile department of a hospital, for example where patients are lying for observation.

It is the purpose of the present invention to indicate a device, a kit of which the device concern and a use of these elements by a method where there is performed a creation of an image of physical conditions in the inner of a bone or behind the bone and preferably in the cranial cavity through a brain scanning, which takes place by use of a signal transducer which outside a sterile area makes possible a continual supervision of the physical condition, which for example may be a blood or a liquid accumulation in the cranial cavity.

According to the present invention this purpose is achieved with a device for fastening in a bone, preferably the cranial bone, for use by continual supervision and examination of physical conditions in the internal cavities of the bone or behind the bone, preferably in the cranial cavity, which device comprises a signal transducer and a guide having an internal hollow space for receiving the signal transducer comprising a signal transmitting and receiving means, preferably an ultrasound transducer in which the guide at the end facing the inner of the bone when using the device is covered by a signal penetrable membrane, and that the guide has engagement means for cooperating with corresponding engagement means on a tool which is used for clamping the guide into a previously drilled hole in the bone.

According to the present invention it is possible to provide the guide in the shape of a screw with a thread which may be brought into engagement with the previously drilled hole. Alternatively, the guide may be provided in the form of a hollow cylindrical plug, which in its cylindrical surface has a boring open to the outer side with a rotatably supported stud having an asymmetrical cross-section with projecting engagement means which by rotation of the stud engages the previously drilled hole.

According to the present invention, there is used a kit as described in the subsequent claims 8, 9 or 10.

According to the invention the above described device and kit for momentary or continuous supervision and examination of the development of blood or liquid accumulations in the cranial cavity, where the signal transducer is provided in the form of an ultrasound transducer, where the crystal is of a kind arranged for creating a three-dimensional image by processing the received/transmitted signals. This technique may, for example, be based on a three-dimensional pulse/ echo image creating method where a wide band wave pulse is used for transmitting, and where rays with different parameters with limited diffraction are used for reception. In such a method, the received signals are processed via fourier-transformation whereby there is created three-dimensional images by a single transmission. Alternatively, application of the device may take place with a signal transducer where the crystal or transducer is rotated between different angular positions, and where the registered signals from each of the angular positions are collected and used for creating a three-dimensional image matrix of the accumulation.

After having bored a hole through the bone, the screw or plug forming a part of the device may be placed very simply and easily. Beside the bored hole, one may possibly provide a relieving hole for pressure equalisation of a possible surpressure which arises at the mounting of the screw. This relieving hole may possibly also be used for introducing liquid and improving the acoustical contact.

If the screw comprises a self-cutting thread there will be achieved an especially simple mounting as you just have to drill a hole with a suitable diameter whereafter the self-cutting thread establishes the thread and thereby the fastening of the screw in the bone. When the screw is located, there is no physical contact between the inner hollow space of the bone and the surrounding environment. There is thus little risk of infection.

It is possible to drill a hole with the same technique which earlier was used in connection with a pressure sensor. When the screw is placed in the bored hole in the cranial bone, this takes place in such a way the signal penetrable membrane is brought into contact with the outer brain membrane.

The screw is arranged very easily by means of the screwing tool which may be of any known kind. Thus, we may be speaking of a screw with a polygonal head which cooperate with a corresponding key. as well as there also may be spoken about a screw with an internal angular cross-section intended to cooperate with a screwing tool of the unbraco type which is placed inside the hollow space of the screw during the screwing.

If the screw and the transducer are made as separate units, the transducer is placed afterwards in the hollow space of the screw. If there is a need for this, the transducer may be applied a gel for achieving a better contact with the signal penetrable membrane. This gel may be placed on a transducer before it is placed in the hollow space of the screw or may be inserted via channels formed between the wall in the hollow space of the screw and the outer side of the transducer.

Between the screw and the transducer, there is provided means which ensure a mutual fixing. This means may be a thread, the bayonet socket click systems, abutting surface/collar or other systems known per se making possible the creation of mutual well-defined positions for those elements. When the crystal of the transducer or the transducer itself is rotated between different positions where there is formed two-dimensional images, it is possible to combine the signals from these positions and create a three-dimensional image matrix which gives a sure indication of the development of an accumulation. Furthermore, there may be performed Doppler-ultrasound of any modality.

The screw may be made of a tissue friendly material, as for example surgical steel. There may also be used plastic. as for example PEEK or POM. However, it is also possible to use other kinds of plastic or metal.

The signal penetrable membrane at the inwards facing end of the screw may be formed of polyester, polycarbonate, or Surlyn. Other materials may also be used. The membrane may have a thickness between about 0.2 mm and 0.8 mm, which gives a sufficiently good ultrasound penetrability.

The membrane is fastened to the screw by bonding, welding or another method of fastening known by itself. Alternatively, screws and membranes are moulded in one piece. In order to ensure the best possible conditions for signals with the purpose refracting and focusing of the signal ray and reduction of so-called side loops, the shape of the membrane is adapted for the transducer.

The membrane may comprise a flexible pad, for example of silicone, natriumchloride. or another signal penetrable material, in order to improve the acoustical contact between the screw and the outer brain membrane.

The tool has a polygonal profile for the purpose of fitting over a corresponding polygonal profile on the screw and has furthermore a fitting handle which makes possible operation with one hand. The tool has preferably a guiding stud fitting into the hollow space of the screw. Hereby the screw is guided during the screwing. If the guide stud has pins or grooves to cooperate with corresponding grooves or pins in the hollow space of the screw, there is achieved a distribution of the forces necessary for the screwing whereby the outer diameter of the screw may favourably be minimised.

In a practical design of the tool, the stud may be provided with 2–4 elongate pins extending over the whole length of the stud and which have a height of about 0.25 mm and a width of about 1 mm. The elongate pins cooperate with corresponding grooves formed in the hollow space of the screw. It is desired to reduce the outer diameter of the screw the most possible in relation to the inner diameter which is determined by the applied transducer.

The outer diameter of the screw is preferably under about 20 mm, preferably down to 12–14 mm. In practice, it has shown that holes in the cranial bone with dimensions under about 20 mm will be closed by themselves.

If the guide is formed as a cylindrical plug there will also be created a hole in the cranial bone with the same technique as described above. Also, plugs could be placed in the hole with the signal penetrable membrane in contact with the outermost brain membrane.

The plug is placed with a slight interference fit in the previously bored hole. The part of the boring in the cylinder wall of the plug open to the outside will be flush with the outside of the asymmetrical stud when this is turned to its inactive position. The stud at its outwards facing end is provided with a notch or a polygonal hole which cooperate with a screw driver, unbraco key, or the like. By rotating the stud, the projecting engagement means are brought out of the open part of the boring and thereby outside the external cylinder surface of the plug. The engagement means are thereby brought into engagement with the wall in the previously bored hole. The engagement means on such a stud may be shaped as threads or as projecting beads penetrating into the bone tissue and thereby clamps and holds the plug.

In the plug the membrane may be formed and fastened as described above in connection with the screw. Thus, it will also be possible to make plug and membrane by moulding in one piece.

The device according to the invention as mentioned above will primarily be used for continual supervision and preferably in neurosurgical departments where a "window" to the cranial cavity is created. The device is especially usable by supervision of the development in liquid or blood accumulations. In order to create a three-dimensional image, the transducer may take a picture, for example for every rotation of 5–10° of the crystal. Hereafter an electronical processing of the formed two-dimensional images takes place in order to establish a three-dimensional image matrix which gives a clear overview of the development of a physical condition in the cranial cavity.

The image processing will usually be performed in a scanner, which is an expensive instrument. According to the invention it will be possible to let the devices form a part of a system which comprises one scanner that arbitrarily may be coupled together with different transducers. Thus, it will be possible with a centrally located scanner to perform a supervision of a larger number of patients who each are provided with a device according to the invention. The scanner may be operated according to a preselected cycle so that a cyclical supervision sequence of a number of patients is performed.

The invention may be used for patients having cranial traumas, for example, because of car accidents, shooting, falling and the like. The device may also be used for patients who have a spontaneous bleeding (aneurysm), for supervising the growth and risk of bursting of the blood vessels. The device may also be used on an operating table, for example by brain surgery where. for example, a tumour is removed. The device makes it possible to get a momentary and sure documentation that all of the tumour is removed. It will also be possible to use the device subsequently by supervising the patient in order to examine if any subsequent bleeding occurs. Oedema may also be localised by use of the device according to the invention. Likewise, it will also be possible to localise a hygroma. Because such hygromas may occur several times in succession, the device will be very suitable for a continuous supervision where a scanning/supervision is performed from time to time.

In practice, it will be possible to use several devices which are placed, for example, in the cranial bone. As the transducers will have a limited cover angle, it will be necessary in certain cases to use two or more transducers. The signals from the two transducers may be combined via software in order to create a single image of the whole cranial cavity.

Alternatively, it will also be possible to produce a transducer where the crystal inside the transducer is movable more than the previously mentioned rotation, thereby to achieve a greater cover angle for the transducer. Today there are commercially available transducers which are so small that transducers could be formed with diameters down to 6–10 mm. If a transducer of a diameter of up to 20 mm is used, where in practice it turns out that the hole may close by itself by forming of connective tissue, it will be possible to use a small crystal which is movable inside the transducer head in order to achieve a great cover angle.

When the device according to the invention is used, the crystal of the transducer will create an image which runs axially in the longitudinal direction of the transducer and the screw. The outwards facing end of the device will be situated outside the surface of the bone. The device may be provided with a point making possible a quick electrical coupling together of the transducer and a scanner. Alternatively, the device may be arranged in such a way that the transducer is detachably mounted in the guide. Hereby, one and the same transducer may be used for supervising several patients provided with a guide.

DESCRIPTION OF THE DRAWING

The invention will hereafter be explained more closely with reference to the attached schematic drawing, where.

Figure 1:
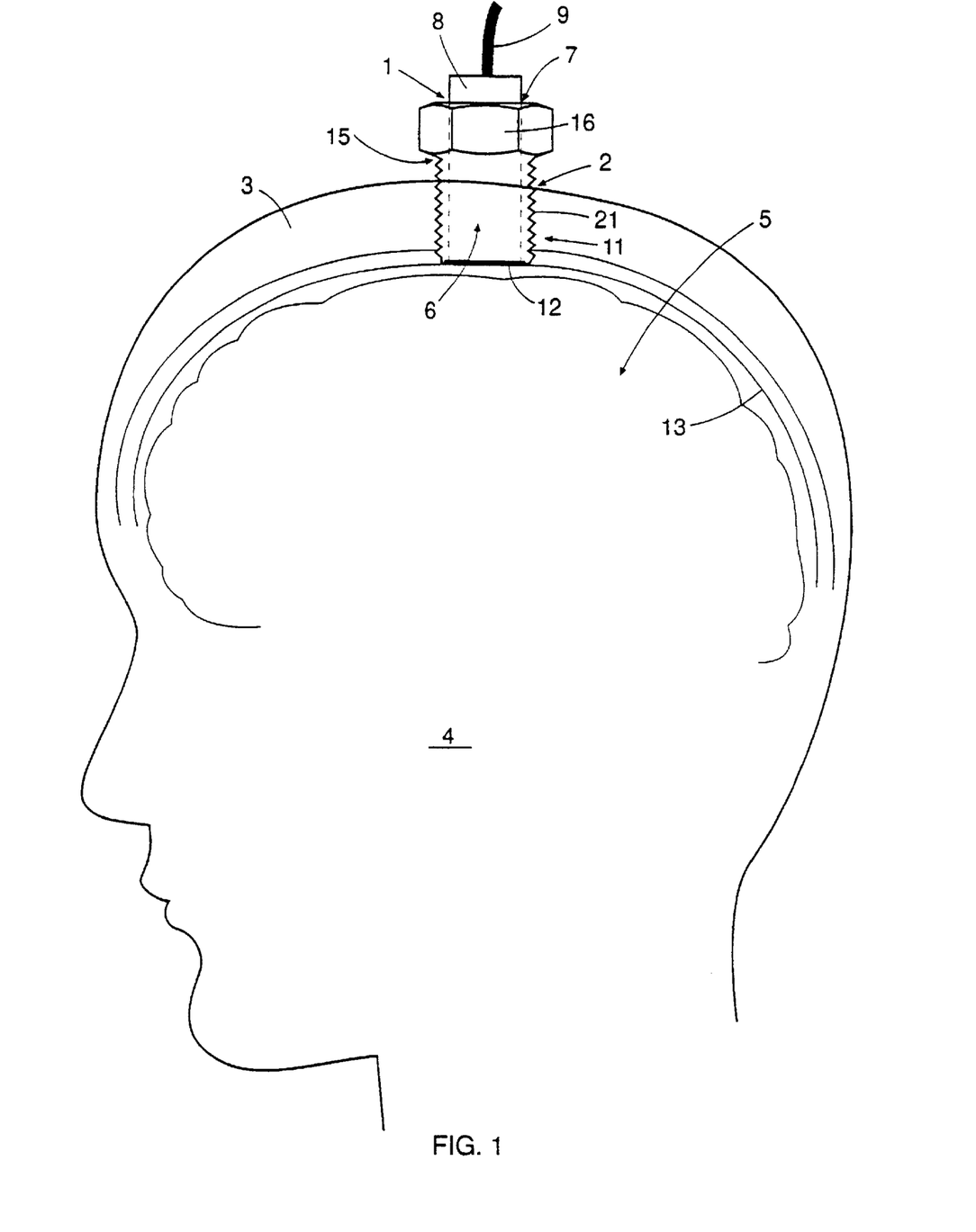
FIG. 1 is a sectional view showing a device according to the invention placed in the cranial bone.

A device 1 is placed in a previously bored hole 2 in a cranial bone 3 on a patient 4 in order to supervise a physical condition in the cranial cavity 5. The device 1 comprises a guide in the form of a threaded screw 6 with an inner boring 7 (see FIG. 2), in which there is mounted an ultrasound transducer 8. The transducer 8 is connected via a wire 9 to a scanner 10 (see FIG. 6) where signal processing is performed and where a three-dimensional image is created when the transducer has taken several two-dimensional images in different rotational positions.

Figure 3:
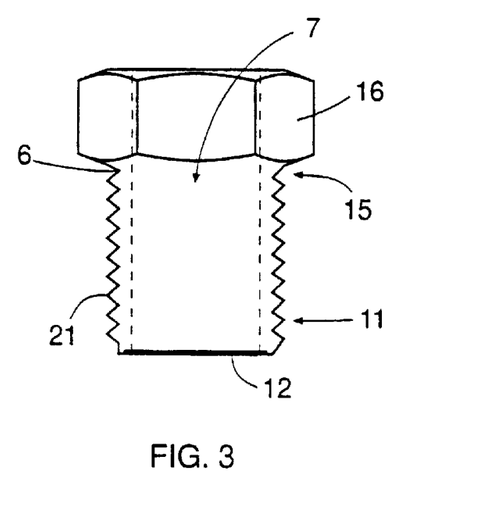
FIG. 3 is a sectional view through the screw shown in FIG. 2.
Figure 4:
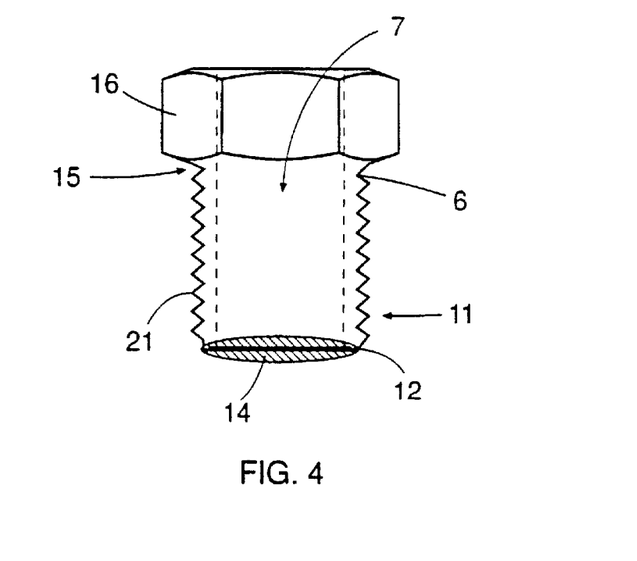
FIG. 4 is a sectional view corresponding to FIG. 3 through another embodiment of the screw.

The screw 6 has at its inwards facing end 11 an ultrasound penetrable membrane 12 which is most clearly seen in FIG. 3 and which covers the boring 2. The membrane 12 is placed in abutment on the outer brain membrane 13. According to an alternative embodiment of the screw 6 it may, as is shown in FIG. 4, comprise a flexible pad 14 which ensures an optimal acoustical contact between the brain membrane 13 and the transducer 8.

Figure 5:
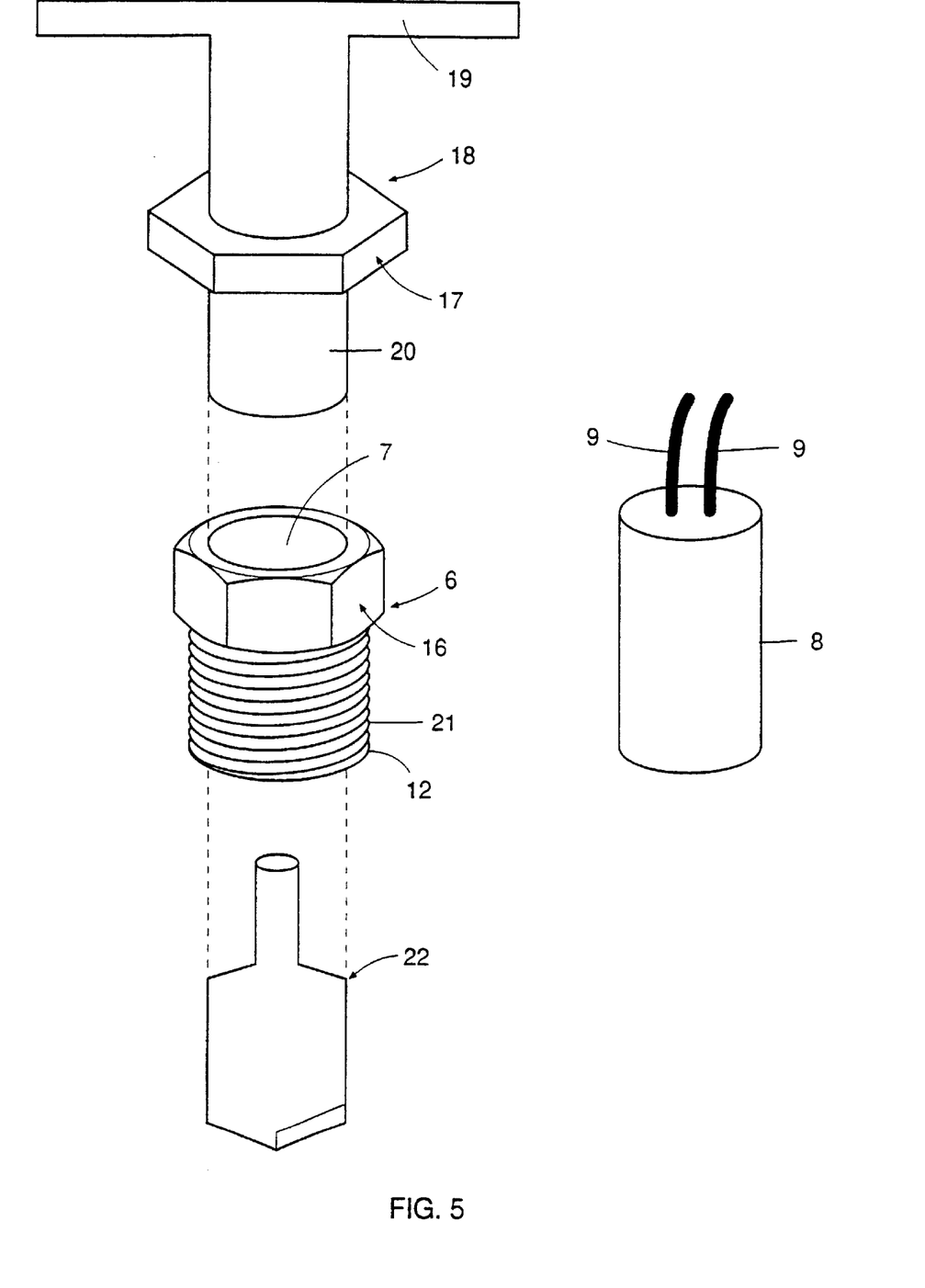
FIG. 5 is a perspective view of a kit according to the invention.

At its outwardly facing end 15, the screw 6 has an externally hexagonal key profile 16 which co-operates with a corresponding external hexagonal profile 17 in a key 18 (see FIG. 5). The key 18 has a handle 19 for operation with one hand and a circular stud 20 which is intended to be placed in the boring 7 of the screw 6 in order to achieve guiding during the screwing of the screw into the hole 2. The stud 20 and the boring 7 may be provided with co-operating axially extended grooves and ribs in order to achieve a distribution of the forces during the screwing. Hereby it becomes possible to minimise the screw 6 and thereby the size of the hole 2.

Figure 2:
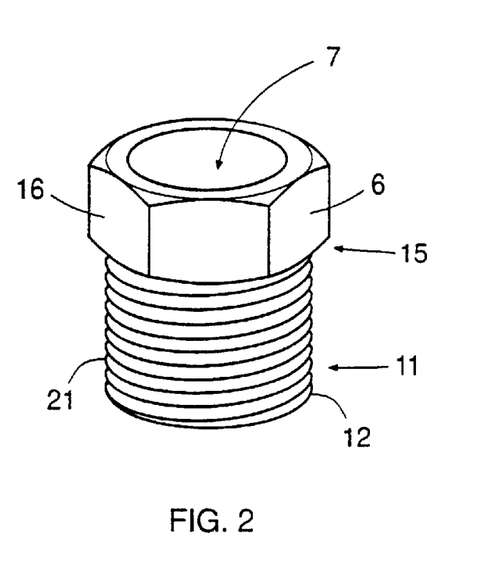
FIG. 2 is a perspective view of a screw forming a part of the device according to the invention.

By using the device, the hole 2 is bored by means of a drill 22 (see FIG. 2). The thread 21 of the screw 6 is self-cutting, and the screw may therefore be located in the formed hole by means of the key 18. Hereafter the hole is closed. When the key 18 is removed, the transducer 8 is placed in the boring 7 of the screw 6, and the device 1 is ready for use. If the screw 6 and the transducer 8 are formed as an integral unit, this unit is mounted by means of a corresponding key, but without a stud 20. Alternatively, it is also possible that the boring 7 of the screw is made with a polygonal cross-section profile and that the key is of the unbraco type with a profile fitting inside the boring.

Figure 6:
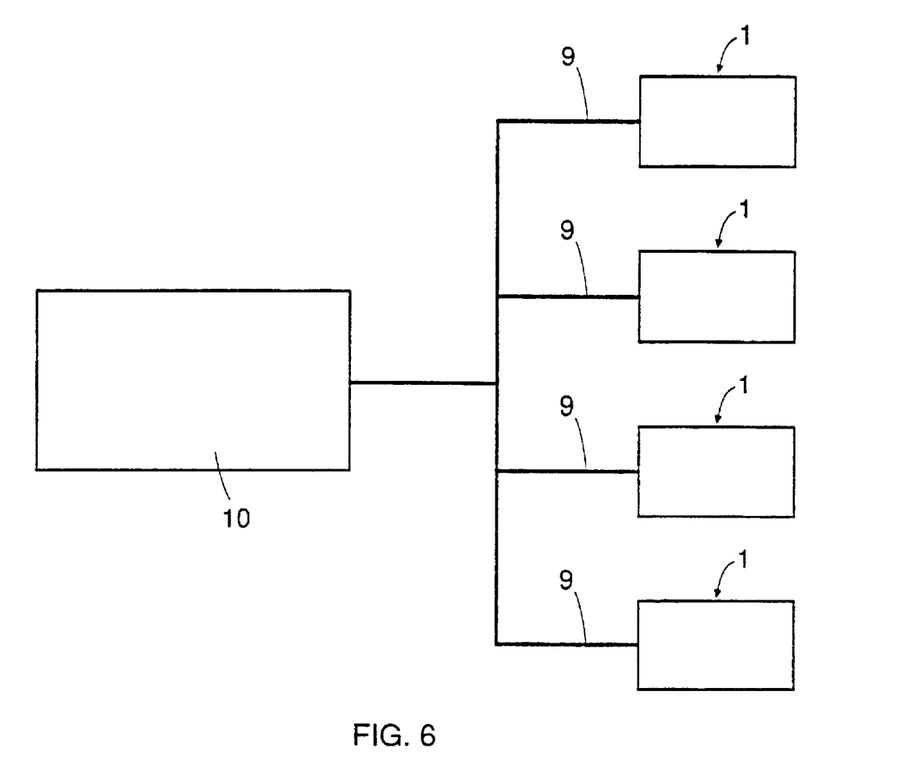
FIG. 6 is a view illustrating a system with several devices according to theinvention which are connected to a single signal processing unit, FIGS. 7–13 a view of different designs of the device including different connecting means.

In FIG. 6 there is seen a system consisting of a central scanner 10 coupled together with a number of devices 1 according to the invention. It will thus be possible to use a single scanner which is a very expensive unit in connection with the supervision of several patients who may be placed in different hospital rooms or hospital departments. In this way certain devices may be placed on neurosurgical departments, while other devices are placed in hospital departments where the patients are admitted for supervision. The shown system may be extended so that the scanner is arranged for automatically giving alarm if a change occurs in the supervised physical condition. The system may be extended in such a way that a cycle is performed automatically, where the single devices 1 are coupled together with the scanner 10. Alternatively, the scanner may be coupled to a single device 1 for constant supervision of a single patient in a given period of time.

Figure 7:
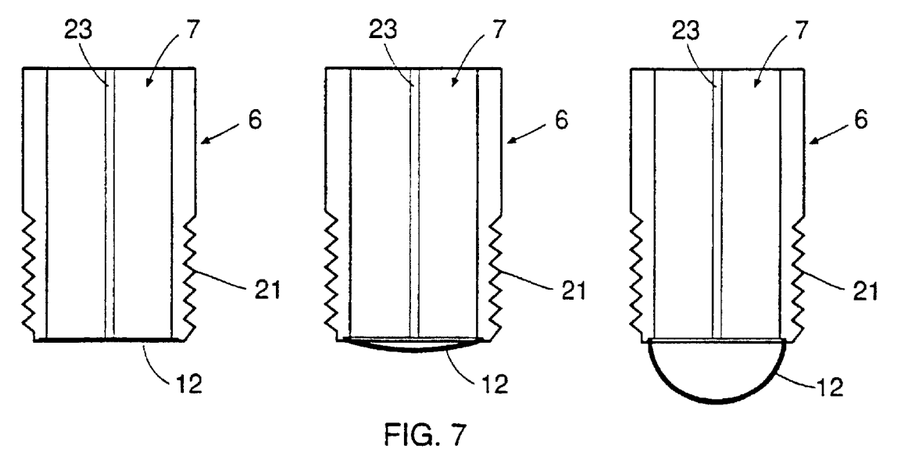

In FIG. 7 there is illustrated three different forms of a screw 6 that form a part of the device according to the invention. From this appears that the membrane 12 may be produced with different shapes. The membrane may thus be plain, as shown to the left, be slightly curved, as shown in the embodiment in the center, or be approximately hemispherical as shown in the right embodiment. The screw 6 in FIG. 7 has axially extending grooves 23 of which only one is shown in FIG. 7. These screws are intended to cooperate with ribs 24 (see FIG. 8) formed on the tool. The tool is thus intended to be inserted into the boring of the screw 7 during the screwing.

Figure 8:
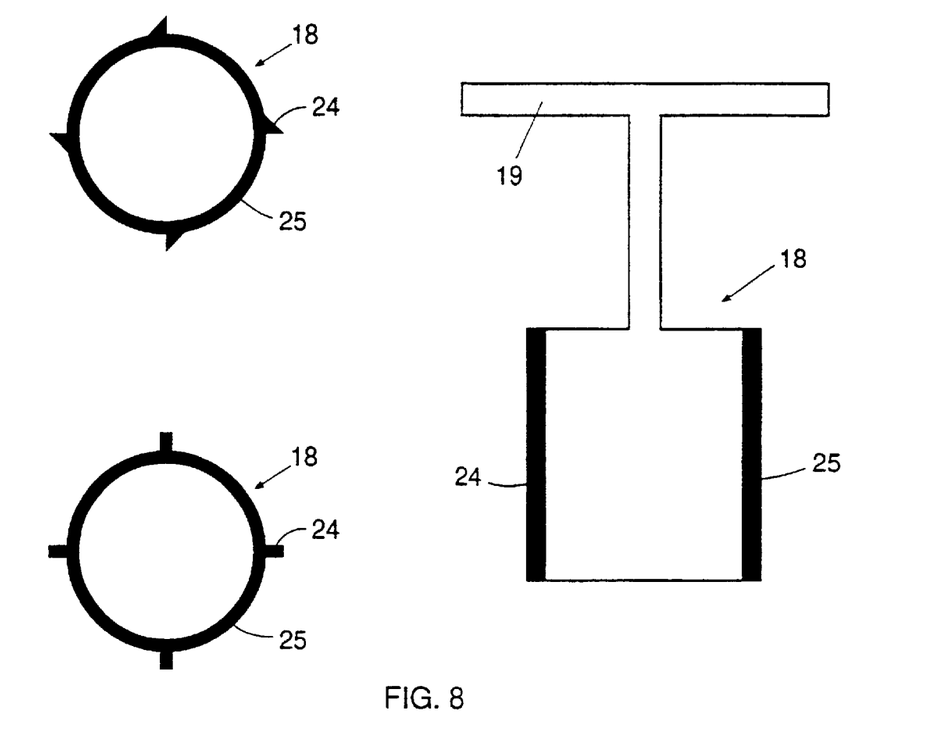
Figure 9:
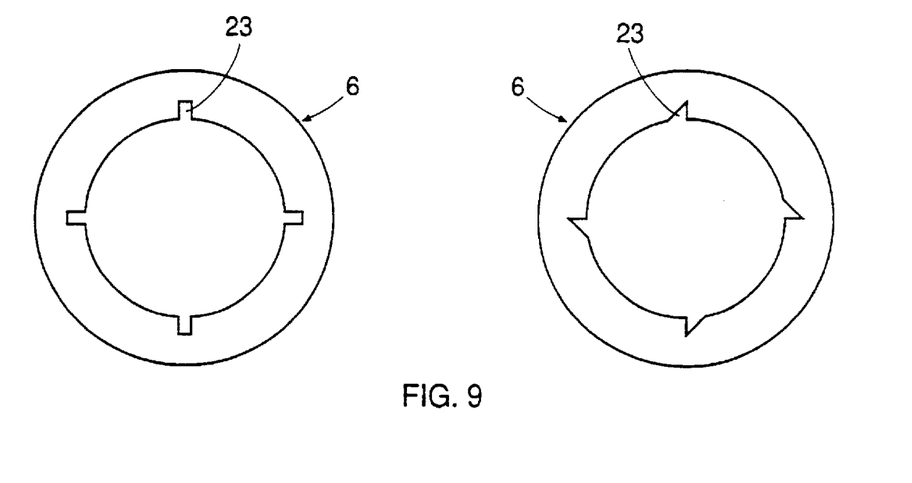

In FIG. 8 there is seen a tool 18. The tool 18 has an engagement part 25 which is provided with ribs 24 that may either have the form shown at the top to the left or at the bottom to the left in FIG. 8. The tool 18 is intended in the shown embodiments to cooperate with the screws 6 having a cross-section as illustrated in FIG. 9, where grooves 23 are formed with a shape and a number corresponding to the shape and number of ribs 24. By using a tool/screw as illustrated in FIGS. 8 and 9. there is achieved a good transmission of torque whereby the wall thickness on the screw 6 may be minimised.

Figure 10:
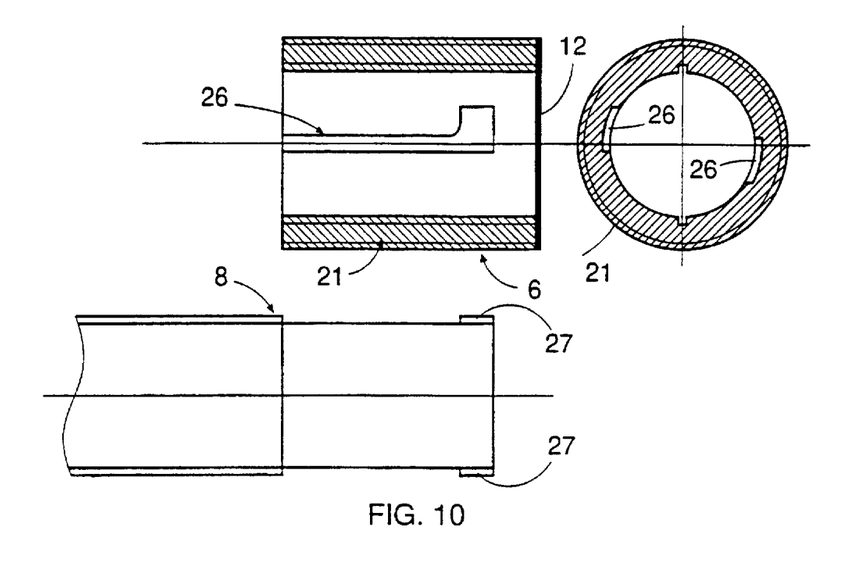

In FIG. 10 there is shown an example of connecting means between the screw 6 and the transducer 8. In FIG. 10 the engagement means is formed by an L-shaped groove 26 in the screw 6 which co-operates with projections 27 on the transducer 8. The groove 26 and the projections 27 act like a bayonet socket.

Figure 11:
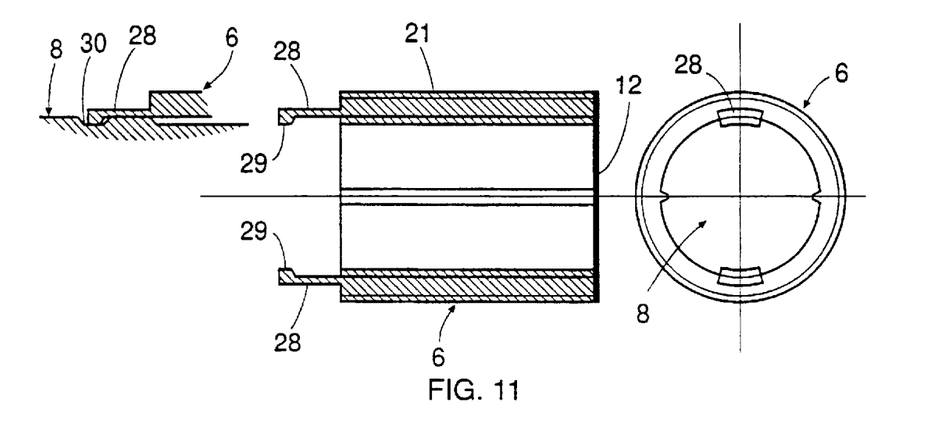

In FIG. 11 there is illustrated another shape of the connecting means between the screw 6 and the transducer 8. Here there is created a snap-coupling consisting of protruding flaps 28 having a projecting part 29 intended for engaging indentations 30 in the transducer 8. The indentation 30 may be a ring-shaped groove or an indentation which gives a mutually rotationally fixed positioning of the screw 6 and the transducer 8.

Figure 12:
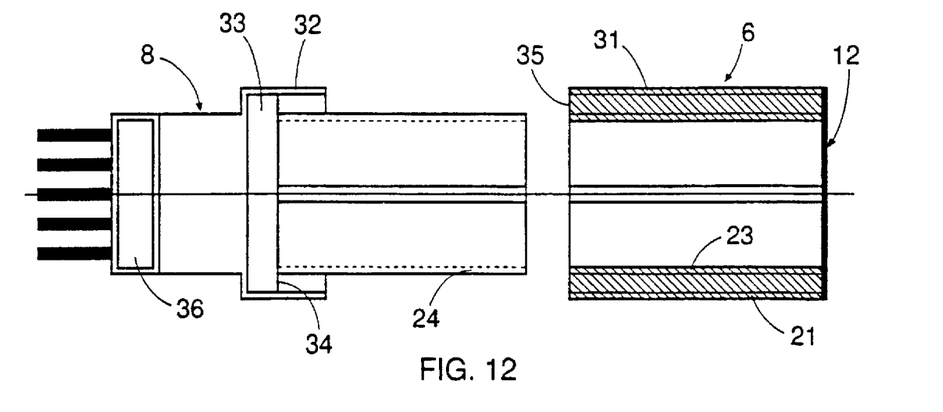

FIG. 12 illustrates a further design of the means to connect the screw 6 and the transducer 8. The screw 6 is provided with a thread 31 co-operating with an internal thread on a nut 32. The nut 32 is fastened at a projecting collar 33 on the transducer 8. The collar 33 has an abutting surface 34 which co-operates with an abutting surface 35 on the screw 6. In the shown form there is created ribs 24 and grooves 23 corresponding to the previously mentioned ribs and grooves. It will thus be possible to connect the screw 6 and the transducer 8 with each other and then screw the screw 6 in the bone by means of a tool which has contact with a plug 36 for the transducer.

Figure 13:
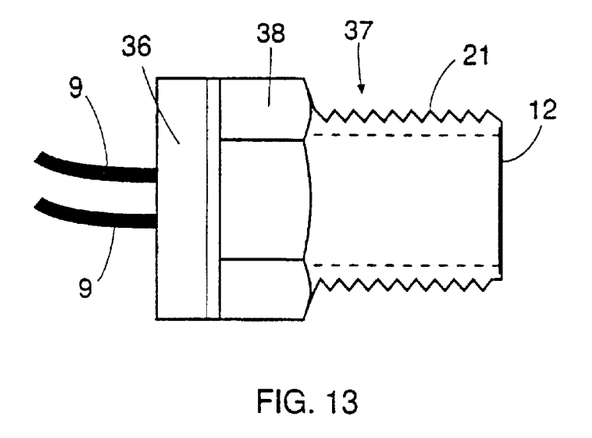

FIG. 13 illustrates a screw and transducer as an integrated unit 37. This unit has a spanner surface 38 for mounting the unit 37. The unit has a plug 36 for connecting the transducer with the wire 9.

Figure 14:
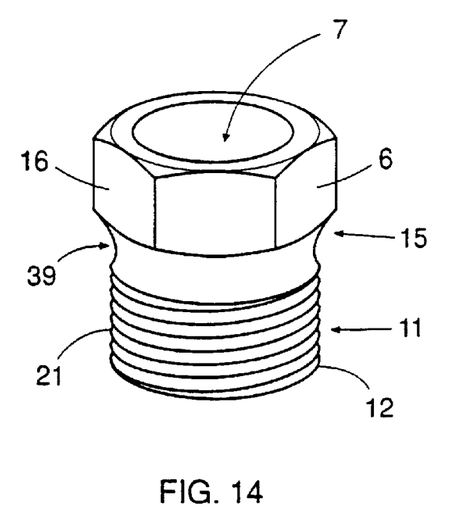
FIG. 14 a perspective view corresponding to FIG. 2 for illustrating a further embodiment of the screw forming a part of the device according to the invention.
Figure 15:
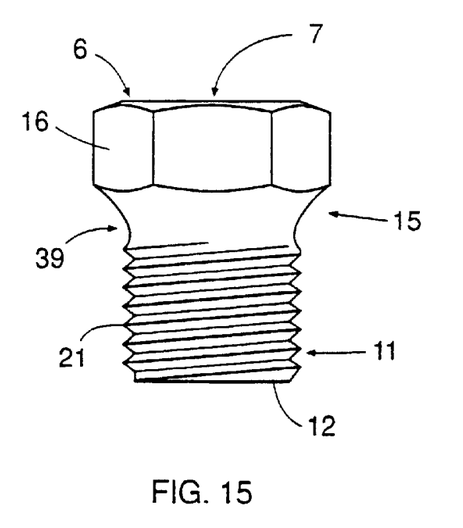
FIG. 15 a lateral view of the screw shown in FIG. 14.

FIGS. 14 and 15 illustrate a screw 6 which mainly corresponds to the screw shown in FIG. 2. This screw, however, differs by being provided with a clearance 39 in the shape of an undercut groove at the outwards facing end 15 of the screw. This clearance 39 is intended to create an area with more space for the skin covering the cranial bone 3. There will thus be a reduced possibility of a reduced irritation on the skin which may be an advantage when the screw has been placed during a longer time for a continual supervision of the physical conditions in the cranium.

As previously indicated, the thread 21 is a self-cutting thread. In such a self-cutting thread there will be transverse grooves with the purpose of breaking the formed chips. These grooves are not illustrated in the schematic drawings. However, it is noted that these grooves will not extend all the way over the length of the thread in order to avoid a possibility of leakage via such grooves. By using the device according to the invention, it is noted that the membrane 12 may be provided in direct abutment on the brain membrane 13. Alternatively, it is also possible to screw the screw 6 in such a depth that the membrane 12 does not abut on the brain membrane. In this situation, the contact with the brain membrane will take place by using a gel which is placed at the outer side of the membrane 12. The screw may possibly be provided with a groove for introducing the gel. Such grooves may also be used to press possible excess amount of gel out through the screw when this is pressed down against the brain membrane at the screwing.

By using the device according to the invention, there will be a need for accommodating to different thicknesses of the cranial bone 3. For this purpose, the screw will be produced with different lengths. In practice, this means that the screw is made with a length between 6 and 14 mm. The screw may, for example, be made with standard lengths of for example, 8, 10 and 12 mm.

Figures 16, 17:
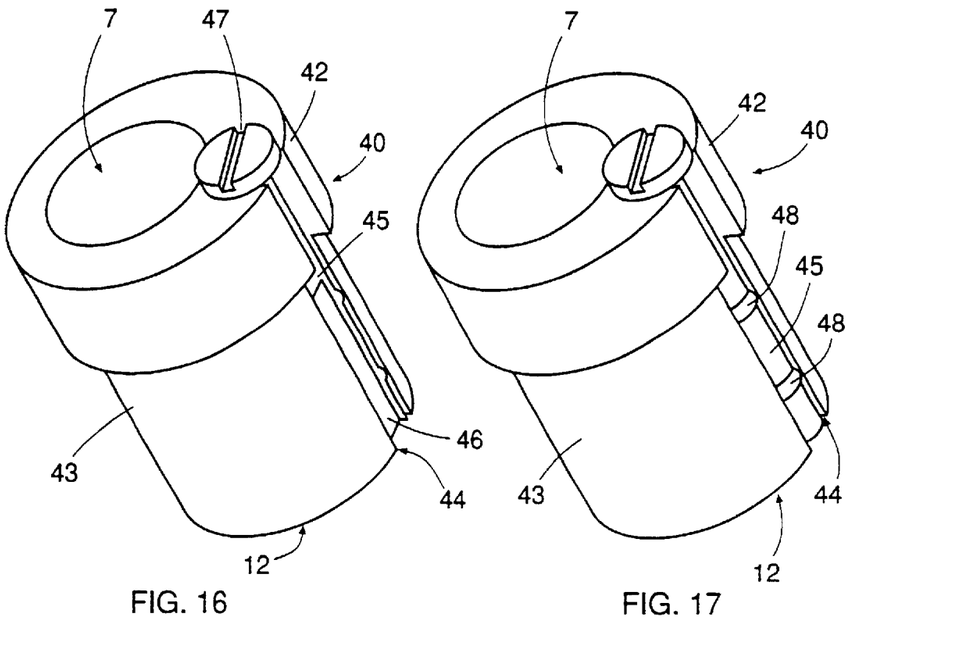
FIGS. 16–17 a perspective view of a cylindrical plug forming a part of the device according to the invention illustrated with engagement means in an inactive position and an active position. respectively, and FIGS. 18–19 a perspective view of a further embodiment of a cylindrical plug forming a part of the device according to the invention illustrated with an engagement means in an inactive position and an active position, respectively.
Figures 18, 19:
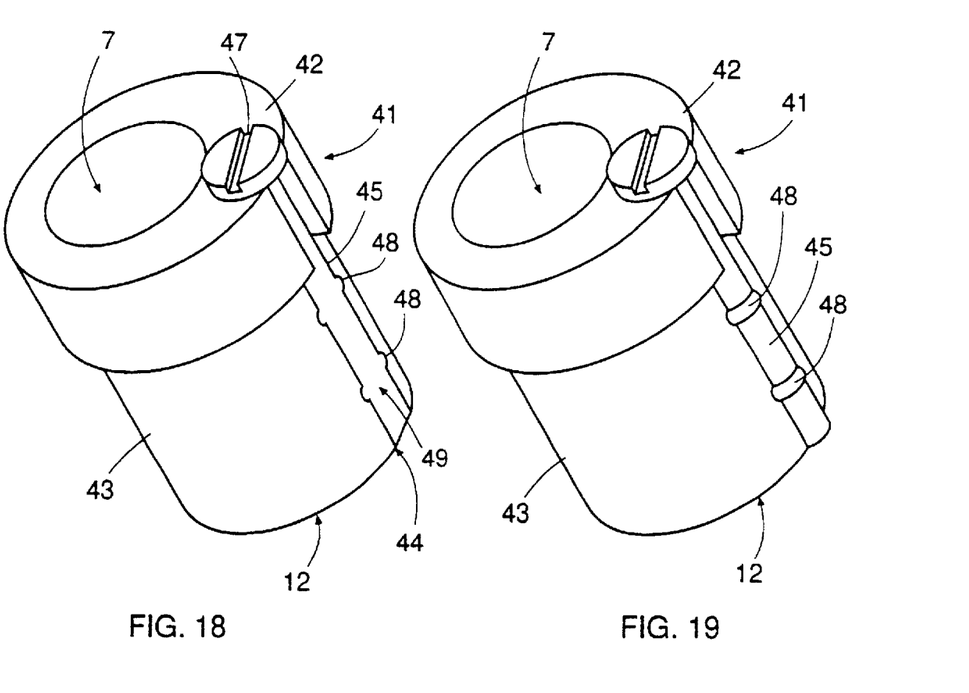

In FIGS. 16 and 17 there is shown a first embodiment of a guide in the shape of a hollow cylindrical plug 40. In FIGS. 18 and 19 there is shown a further embodiment of a cylindrical plug 41.

The plug 40 has a head 42 and a cylindrical stem 43. The cylindrical stem 43 is intended to be placed in a correspondingly dimensioned boring in a cranial bone 3. The plug contains an inner boring 7 for receiving a transducer 8. The plug is provided with a boring 44 in its cylinder surface. in which boring there is received a pin 45. The boring 44 is placed so that it is open to the outside of the cylinder surface. The pin 45 is made with a chamfered surface 46. The pin will thus, when the chamfered surface 46 faces outwards, be flush with or be situated within the cylinder surface as defined by the stem 43 of the plug.

When the pin 45 by means of a screwdriver is brought into engagement with notch 47, is rotated from the position shown in FIG. 16 to the position shown in FIG. 17, the projecting beads 48 which constitute engagement means, will be turned outside the cylinder surface and brought into engagement with the cranial bone. Thereby the plug 40 is clamped and held in the cranial bone. With this embodiment, the risk of bone splinters arising by thread cutting is avoided.

The plug 40 may be made of a material where at least the surface is elastically resilient with the purpose of achieving a firm interference fit and thereby a sealing in the cranial bone. The pin 45 may be established with a fit so that leakages do not occur. Attentively. an O-ring may be placed between the pin 45 and the boring 44.

The embodiment illustrated in FIGS. 18 and 19 differ by the pin 45 having a plane surface 49 which has a considerably greater extension than the plane surface 46. The surface 49 thus extends over all of the length of the pin. Furthermore, the boring 44 is off-set further outwards in the cylinder surface so that it is not only the beads 48 which appear outside the cylinder surface of the stem 43. A part of the cylinder surface of the pin will likewise be situated outside the cylinder surface of the stem and thereby create a greater penetration into the cranial bone. Hereby there is achieved a greater clamping force and a security against rotation of the plug 41 in the hole in the cranial bone.

A plug 40, 41 according to the invention may be made with a length as explained above in connection with the screw. Furthermore, the membrane 12 may be provided in different embodiments as explained above in connection with the screw 6.

What is claimed is:

1. A device adapted to be fastened in a bone, preferably the cranial bone for use in continual supervision and examination of physical conditions in the internal cavities of the bone or behind the bone, preferably in the cranial cavity which device comprises a signal transducer and a guide having an internal hollow space for receiving the signal transducer and that the guide has engagement means for co-operating with corresponding engagement means on a tool which is used for clamping the guide into a previously drilled hole in the bone, the signal transducer comprising an ultrasound transducer wherein the distal end of the guide which in use faces the inner of the bone, is covered by an ultrasound signal penetrable membrane.

2. A device according to claim 1, wherein the guide is provided in the form of a screw having a thread that may engage the previously drilled hole.

3. A device according to claim 1, wherein the guide is provided in the shape of a hollow cylindrical plug which in its cylindrical surface has a boring open to the outer side with a rotatably supported stud having an asymmetrical cross-section with projecting engagement means which by rotation of the stud engages the previously drilled hole.

4. A device according to claim 1, wherein the guide and the transducer are provided with co-operating coupling means for holding the transducer in a predetermined position in the guide and thus relative to the bone, which coupling means are selected among bayonet sockets, threaded connections, and snap locks.

5. A device according to claim 1, wherein the signal transmitting and receiving means of the transducer is rotatable by at least 180° about an axis parallel to the longitudinal axis of the guide.

6. A device according to claim 1, wherein the guide and the membrane are moulded as one single piece.

7. A device according to claim 1, wherein the engagement means is a self-cutting thread and that the guide is arranged to cooperate with a bored hole which is less than 20 mm.

8. A kit for use in continuous supervision and examination of physical conditions inside the inner cavity of a bone or behind the bone, preferably in the cranial cavity and preferably for indicating a possible development in accumulations of blood and/or liquid under conditions, where a sterile condition during the supervision is not required, and where a full anesthesia is not required, comprising:

(a) a drill for forming a bored hole in the bone, (b) a device according to claim 1 and comprising a screw having a self-cutting thread and which is dimensioned according to the formed bored hole, and which has a boring extended in the longitudinal direction of which one end is covered by the signal penetrable membrane, (c) a tool for screwing the screw as means on the tool are designed for engaging co-operating means on the screw, and (d) the signal transducer which is arranged to be received in the boring of the screw with the transducer abutting on the membrane.

9. A kit according to claim 8 wherein the screw has a polygonal profile co-operating with a corresponding polygonal profile on the tool and wherein the tool comprises a stud intended to engage the boring for guiding the screw during the screwing.

10. A kit for use by continual supervision and examination of physical conditions inside the inner cavity of a bone or behind the bone preferably in the cranial cavity and preferably for showing a possible development in accumulations of blood and/or liquid under conditions, where a sterile condition during the supervision is not required, and where a full anesthesia is not required, comprising:

(a) a drill for forming a bored hole in the bone, (b) a device according to claim 1 and comprising a hollow cylindrical plug having in its cylinder surface a boring open to the outer side with a rotatably supported stud and having an outer diameter dimensioned according to the formed bored hole, the inner hollow space of which at one end is covered by the signal penetrable membrane, (c) a tool for rotating the stud so that projecting co-operating means are brought outside the open boring in the cylinder surface as means on the tool are designed to engage co-operating means on the stud in a rotationally fixed connection, and (d) the signal transducer which is arranged for being received in the boring of the plug with the transducer abutting on the membrane.

11. A use of a device according to claim 1 momentary or continual supervision and examination of the development of accumulations of blood or liquid in the cranial cavity, where the signal transducer is provided in the form of an ultrasound transducer which has a crystal for creating a three-dimensional image by processing the received/transmitted signals.

* * * * *